Figure 1:
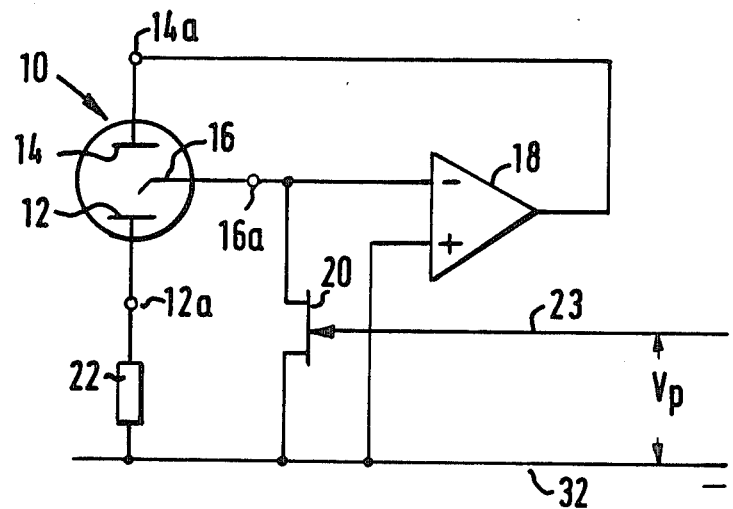

United States Patent [19]

Jones et al.

[11] Patent Number: 4,776,203

[45] Date of Patent: Oct. 11, 1988

[54] GAS MONITOR CIRCUITS

[75] Inventors: Gareth J. Jones, Great Abington; Howard A. Buckenham, Brentwood; Paul Gotley, North Weald, all of United Kingdom

[73] Assignee: Neotronics Limited, Hertfordshire, United Kingdom

[21] Appl. No.: 919,270

[22] Filed: Oct. 16, 1986

[30] Foreign Application Priority Data

Oct. 18, 1985 [GB] United Kingdom ............... 8525694

[51] Int. Cl.⁴ .......................................... G01N 31/00
[52] U.S. Cl. ...................................... 73/23; 307/550; 307/568
[58] Field of Search ....................... 73/19, 23; 204/424, 204/412, 1 T; 357/25; 422/98; 338/34; 307/501, 550, 568

[56] References Cited

U.S. PATENT DOCUMENTS 3,818,244  6/1974  Dolby et al. .................. 307/550
4,013,975  3/1977  Kataoka ....................... 307/568
4,227,984  10/1980  Dempsey ....................... 204/424

OTHER PUBLICATIONS

Sabre, leaflet advertising Toxiguard 1/R sensor (Sabre Gas Detection, Ltd.): date of publication unknown but prior to Oct. 18, 1985.

*Primary Examiner*—Michael J. Tokar
*Attorney, Agent, or Firm*—Dennis P. Clarke

[57] ABSTRACT

Circuits are described in which the sensing and the reference electrodes of a gas sensor housed within a gas monitor are connected together through the source and the drain of a field effect transistor (FET). The gate of the FET is connected to a power source to apply a first voltage to the gate when the monitor is operational and a second voltage, which is preferably zero, when the monitor is not operational, the resistance between the source and the drain of the FET being low when the second voltage is applied to the FET gate so that the sensing and reference electrodes are connected together in a short circuit. When the first voltage is applied to the FET gate, however, the short circuit is effectively broken. The circuit has output lines leading to an output device, e.g. for displaying information or an alarm. A resistor of large resistance is connected between the two output lines and, when a gas is sensed a large voltage change occurs across the resistor which can be used directly, i.e. without an intervening amplifier, for driving the output device. A further, small resistor is connected between the reference electrode and the sensing electrode to provide noise immunity to the circuit.

12 Claims, 2 Drawing Sheets

GAS MONITOR CIRCUITS

The present invention relates to gas monitors and particularly to improvements in the electronic circuits thereof.

Gas monitors are instruments that detect a gas and provide a visual or audible output according to the amount of gas sensed. Each monitor includes one or more replaceable sensors providing an electronic signal proportional to the amount of gas detected which signal is analyzed by circuitry within the monitor to give the desired output. The output may be a display, in analog or digital form, of the amount of a specific gas detected and/or it may be a printer or plotter and/or an alarm to give an audible and/or visible warning if the concentration of a gas falls to an undesirable level or if the concentration of a gas rises above a certain set threshold level. However, gas monitors need not necessarily give a direct indication of the amount of gas detected but may use the signal from one or more sensors to compute another parameter which may be displayed or printed etc.

The replaceable sensors used in the sensors of the present invention are of the type having a sensing (or working) electrode for sensing the gas, a counter electrode and a reference electrode which are connected via terminals to the circuitry within the monitor. The potential difference between the sensing electrode and the reference electrode must be controlled and in some sensors this is done by connecting these two electrodes to the two inputs of an operational amplifier either directly or through a resistor. Examples of such an arrangement can be found in British Patent Specification Nos. 1,101,101 and 1,385,201 and in U.S. Pat. No. 3,776,832.

When the monitor is not being used, the sensing and reference electrodes of a sensor are customarily connected together in a short circuit, optionally via a resistor, in order to ensure that the monitor will produce reliable readings quickly after it has been started up. It is of course necessary to break such a short circuit when the monitor is started up and while it is operational. Hitherto, the making and breaking of the short circuit has been achieved either by a relay which breaks the short circuit automatically when the monitor is started up or by a manually operated switch.

The present invention provides improvements in the circuit of gas monitors and in particular greatly simplifies the circuit and makes it more efficient, more reliable and cheaper.

Each of FIGS. 1, 2, 3 and 4 are schematic diagrams of circuits comprising the alternative embodiments of the gas monitor of the present invention.

According to the present invention, there is provided a gas monitor comprising a first terminal for electrical connection to the sensing electrode of a gas sensor, a second terminal for electrical connection to the reference electrode of the gas sensor, a field effect transistor (FET) having a drain, a source and a gate and being connected via the drain and the source between the first and second terminals and means for applying a first voltage $V_p$ between the gate and either the drain or the source of the transistor when the monitor is operational, and a second voltage, which preferably is zero, when the monitor is not operational, the arrangement being such that the resistance of the transistor between the drain and the source is sufficiently low when the second voltage is applied to provide a short circuit between the two terminals and sufficiently high to break the short circuit when the first voltage $V_p$ is applied.

By using an FET, the short circuit is broken automatically on start-up, i.e. when the monitor is switched on, and the short circuit is re-established automatically when the monitor is switched off; the advantage of using an FET as compared to other sorts of transistor is that the short circuit will be maintained even if the monitor is not connected to a power source. In contrast to the switch or relay used hitherto, the FET has no contacts that can become dirty and hence cause a breakdown in the monitor. In addition, an FET can be built into a printed circuit board simply and it is a cheaper component than a switch or a relay and accordingly the arrangement of the present invention is cheaper and simpler to manufacture than the known arrangements.

The FET is preferably selected on the following criteria:

(1) low resistance between its drain and source when the second voltage is applied, which second voltage is preferably zero; this resistance is preferably less than 1000 ohms, e.g. 100 to 500 ohms, and (2) a low leakage current when the first voltage $V_p$ is applied, in which case the resistance should be such that the leakage current is ideally less than 100 nanoamps, e.g. less than 50 nanoamps and preferably less than 20 nanoamps.

If the numerical limitations given in conditions (1) and (2) are not met completely, the monitor will still work but it will have a longer start-up time and/or a high zero current; a "zero current" is the current flowing when there is no gas of the type to be detected at the sensing electrode of the sensor.

It is evident that the FET must be such that the first voltage $V_p$ between the gate and either the drain or the source of the FET must be low enough to be supplied by the power source of the monitor.

The FET may be an n-channel or a p-channel type.

As well as the FET, the first and second terminals of the monitor may be connected through other electronic elements, e.g. a resistor, so long as the other elements do not alter the effect of the FET described above.

The present invention is also concerned with the electrical signal that gives a measure of the amount of gas present at the sensing electrode of a gas sensor. According to British Patent Specification No. 1,101,101, this electrical signal is derived by measuring the voltage drop across a resistor connected in series with the sensing electrode. The value of the resistance must not be too high or else the response time of the sensor is unacceptably high and it must not be too low or else the change in voltage on sensing a gas is small and hence measurements are difficult to obtain and inaccurate. Furthermore, as the value of the resistance is reduced, the sensing system becomes more prone to noise. To overcome these problems an intermediate value resistor is chosen that results in an acceptable response time and noise immunity, but the voltage change is still too low, typically 10 microvolts per part per million of gas, to provide a useful output, for example for driving a display, for triggering an alarm or that can be plotted on a graphical plotter. The voltage drop across the resistor is therefore amplified by an amplifier which has a gain of several hundred fold to a required level but this makes the output circuit sensitive to noise and to fluctuations due to temperature variations and other factors. The present invention overcomes the problem of using an operational amplifier to boost the output voltage.

According to the present invention, there is provided a gas monitor having terminals for providing electrical connection to the sensing-, the counter- and the reference-electrodes of a gas sensor, which monitor comprises:

an operational amplifier having inputs connected to the sensing- and reference- electrode terminals and an output connected to the sensing electrode terminal or to the counter electrode terminal, which output provides a signal in accordance with the amount of gas sensed by the sensing electrode, two output lines one of which is connected either to the sensing electrode terminal or to the counter electrode terminal, a resistor connected between the output lines but which is not connected in series between the sensing electrode and the amplifier, and means for detecting the voltage difference between the output lines which provides a measure of the amount of gas sensed at the sensing electrode.

In order to provide noise immunity, the monitor may include a further resistor having a lower resistivity than the resistor connected between the output lines, which further resistor is connected in series between the sensing electrode and one of the inputs of the operational amplifier. Thus, one resistor can be chosen to optimise the trade-off between noise immunity and a fast response time while the output of the gas sensor is measured as the voltage drop across the other resistor. By making the resistor between the output lines highly resistive, a large voltage drop is generated across the second resistor which is sufficiently large to provide a direct output, i.e. it is not necessary to provide an operational amplifier to boost the output voltage. This is possible because the impedance between the inputs of the operational amplifier is high as is the impedance of the measuring means.

The present invention will now be described, by way of example only, with reference to FIGS. 1 to 4 of the accompanying drawings all of which show gas monitor circuits in accordance with the present invention.

Figure 2:
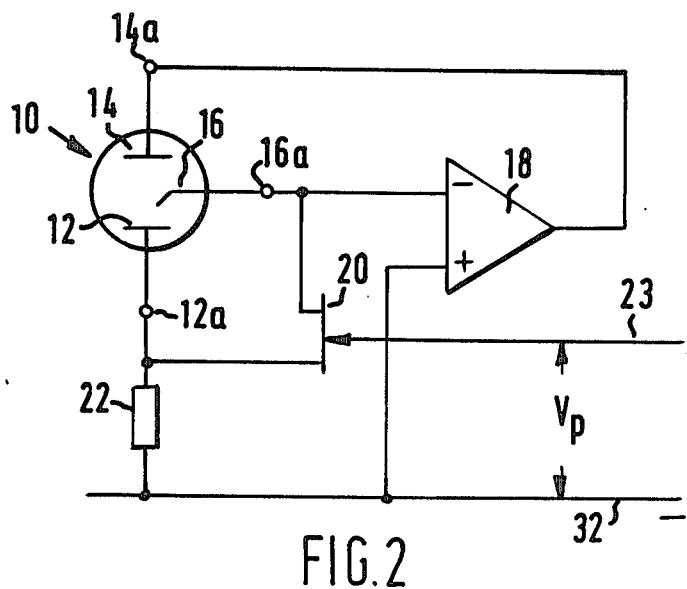

In FIG. 1, a gas sensor 10 is shown having a sensing electrode 12, a counter electrode 14 and a reference electrode 16 connected to terminals 12a, 14a and 16a respectively of a gas monitor. The reference electrode 16 is connected to the negative input of an operational amplifier 18, and also to the source of a field effect transistor (FET) 20. The sensing electrode 12 is connected through a resistor 22 to a line 32 and the drain of the FET 20 is either connected directly to line 32 (FIG. 1) or between the sensing electrode 12 and the resistor 22 (FIG. 2). A voltage $V_p$ is applied to the gate of the FET 20 via line 23 when the gas monitor is operational but no voltage is applied when the monitor is not operational. When no voltage is applied to the FET, the resistance between the drain and the source of the FET is small (a few hundred ohms) and so the sensing and reference electrodes are effectively shorted together. When in operation, the monitor applies a voltage $V_p$ to the gate of the FET which causes the resistance between the source and the drain of the FET to increase to a high value at which the leakage current between the drain and source is at most 100 microamps but generally it should be of the order of tens of nanoamps. This removes the short circuit between the sensing and the reference electrodes.

The FET 20 may be an n-channel FET, in which case voltage $V_p$ must be negative with respect to the drain or the source or a p-channel device, in which case the voltage $V_p$ must be positive. The use of an FET to short circuit the sensing and reference electrodes together when the monitor is not switched on and to break the short circuit automatically when the monitor is operational greatly simplifies the circuitry and makes it much cheaper.

Figure 3:
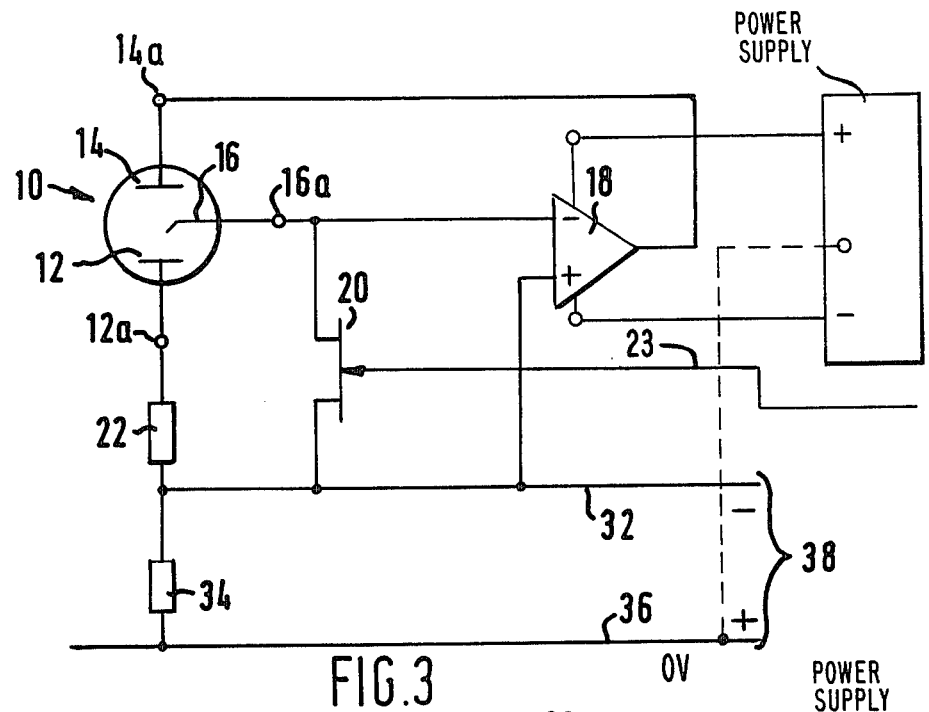
Figure 4:
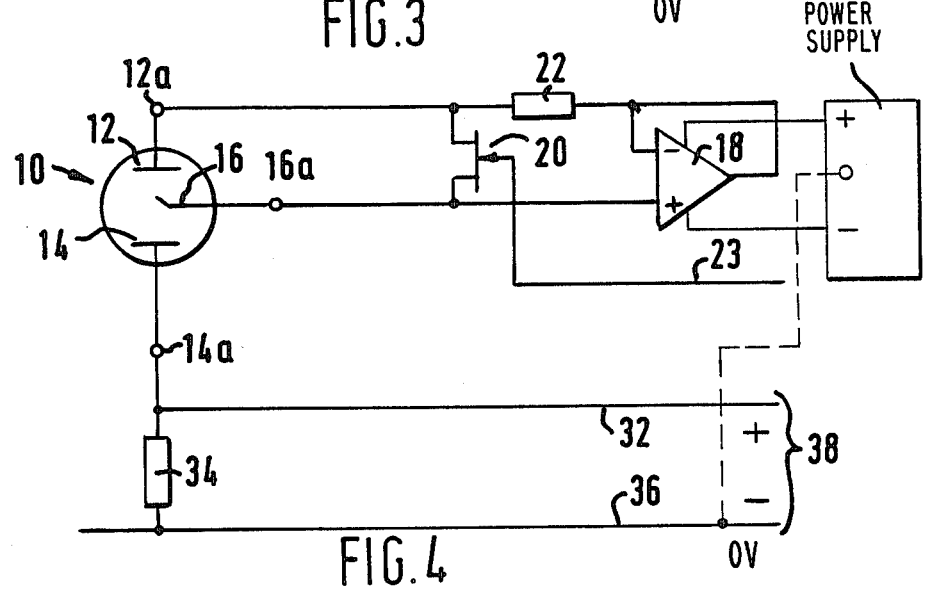

Two further circuits according to the invention are shown in FIGS. 3 and 4, in which the same reference numerals are used as in FIG. 1 to indicate identical elements. In the FIG. 3 circuit, the reference electrode 16 is connected to the negative input of an amplifier 18, while the output of the amplifier is connected directly to the counter electrode 14. A first resistor 22 is connected between the sensing electrode 12 and a first output line 32 and a second resistor 34 is connected between the first output line and a second output line 36. The positive input to the amplifier is connected to the first line 32. The voltage drop across the second resistor 34 is measured through output lines 32 and 36 by a measuring device 38 of high impedance which may be a display, a printer, a plotter or an alarm trigger.

The FIG. 4 circuit contains the same components fulfilling the same function as those of the FIG. 3 circuit and therefore the same reference numerals have been used in both Figures.

When gas is present at the sensing electrode, a potential difference is established between the sensing and reference electrodes and hence between the inputs of operational amplifier 18 causing a current to flow at the amplifier output and hence also between the sensing and counter electrodes, the magnitude of which is proportional to the amount of gas present at the sensing electrode. Because the impedance between the terminals of an operational amplifier is large and because the measuring device 38 is also of high impedance, the current that is caused to flow through the resistor 34 is approximately the same as that flowing through the sensor cell. By using a resistor 34 of high resistance, a large voltage drop between lines 32 and 36 can be achieved which is sufficient to drive a printer or display 38 directly without using an operational amplifier. The resistor 34 may have a resistance of 0.5 to 500 kohms, preferably 1 to 100 kohms. For example, when resistor 34 has a resistance of 10 kohms, the voltage drop across resistor 34 may be approximately 1 mV per part per million of gas detected. Resistor 22 has a resistance of between 0 and 200 ohms and provides noise immunity to the circuit by altering the relative potentials between the sensing- and the counter- electrodes in response to noise. The low resistivity of the first resistor 22 also provides a fast response time.

We claim:

1. A gas monitor comprising a first monitor terminal for electrical connection to the sensing electrode of a gas sensor, a second monitor terminal for electrical connection to the reference electrode of the gas sensor, a field effect transistor (FET) having a gate terminal, a source terminal and a drain terminal and being connected via the drain and the source terminals between the said first and second monitor terminals and means for applying a first voltage $V_p$ between the gate terminal and one of the other terminals of the transistor when the monitor is operational, and a second voltage when the monitor is not operational, the arrangement being such that the resistance of the transistor between the drain terminal and the source terminal is sufficiently low when the second voltage is applied to provide a short circuit between the two monitor terminals and sufficiently high to break the short circuit when the first voltage $V_p$ is applied.

2. A monitor as claimed in claim 1, wherein the FET has a resistance of less than 1000 ohms between its drain terminal and its source terminal when the second voltage is applied.

3. A monitor as claimed in claim 2, wherein the said resistance of the FET is in the range of from 100 to 500 ohms.

4. A monitor as claimed in claim 1, wherein the second voltage is, in operation, zero.

5. A monitor as claimed in claim 1, wherein, when the the first voltage $V_p$ is applied, the resistance of the FET is such that the leakage current between the said drain terminal and the said source terminal is less than 100 nanoamps.

6. A monitor as claimed in claim 5, wherein the said leakage current is less than 50 nanoamps.

7. A monitor as claimed in claim 6, wherein the said leakage current is less than 20 nanoamps.

8. A monitor as claimed in claim 1, wherein a resistor is connected between the sensing electrode terminal and the FET.

9. A gas monitor having terminals for providing electrical connection to the sensing-, the counter- and the reference-electrodes of a gas sensor, which monitor comprises:
   an operational amplifier having inputs connected to the sensing- and reference- electrode terminals and an output connected to the counter electrode terminal,
   two output lines one of which is connected to the sensing electrode terminal,
   a resistor which is connected between the two output lines but which is not connected in series between the sensing electrode terminal and the amplifier, and
   means for detecting the voltage difference between the output lines which provides a measure of the amount of gas sensed at the sensing electrode.

10. A monitor as claimed in claim 9, which includes a further resistor having a lower resistivity than the resistor connected between the output lines, which further resistor is connected between the sensing electrode terminal and the sensing electrode input of the operational amplifier.

11. A gas monitor having terminals for providing electrical connection to the sensing-, the counter- and the reference-electrodes of a gas sensor, which monitor comprises:
   an operational amplifier having inputs connected to the sensing- and reference- electrode terminals and an output connected to the sensing electrode terminal,
   two output lines, one of which is connected to the counter electrode terminal,
   a resistor which is connected between the two output lines but which is not connected in series between the sensing electrode terminal and the amplifier, and
   means for detecting the voltage difference between the output lines which provides a measure of the amount of gas sensed at the sensing electrode.

12. A monitor as claimed in claim 11, which includes a further resistor having a low resistivity than the resistor connected between the output lines, which further resistor is connected between the sensing electrode terminal and the sensing electrode input of the operational amplifier.

* * * * *